(12) United States Patent
Tong et al.

(10) Patent No.: US 7,872,744 B2
(45) Date of Patent: Jan. 18, 2011

(54) VISUAL INSPECTION APPARATUS FOR FLEXIBLE PRINTED CIRCUIT BOARDS

(75) Inventors: Lian-Da Tong, Shenzhen (CN); Ching-Hung Pi, Taoyuan (TW); Cheng-Ta Tu, Taoyuan (TW); Yin-Kui Zhu, Shenzhen (CN)

(73) Assignees: FuKui Precision Component (Shenzhen) Co., Ltd., Shenzhen, Guangdong Province (CN); Foxconn Advanced Technology Inc., Tayuan, Taoyuan (TW)

( * ) Notice: Subject to any disclaimer, the term of this patent is extended or adjusted under 35 U.S.C. 154(b) by 466 days.

(21) Appl. No.: 12/110,540

(22) Filed: Apr. 28, 2008

(65) Prior Publication Data
US 2009/0033925 A1 Feb. 5, 2009

(30) Foreign Application Priority Data
Aug. 3, 2007 (CN) .......................... 2007 1 0075617

(51) Int. Cl.
*G01N 21/00* (2006.01)

(52) U.S. Cl. .................................. 356/237.5; 356/237.4
(58) Field of Classification Search ....................... None
See application file for complete search history.

(56) References Cited

FOREIGN PATENT DOCUMENTS

| CN | 1513746 A | 7/2004 |
|---|---|---|
| JP | H01-227970 A | 9/1989 |

*Primary Examiner*—Gregory J Toatley
*Assistant Examiner*—Amanda H Merlino
(74) *Attorney, Agent, or Firm*—Andrew C. Cheng

(57) ABSTRACT

An exemplary visual inspection apparatus for a flexible printed circuit board includes a frame, an inspection station, a control system, a roller system and a power system. The inspection station is disposed on the frame. The inspection station has an inspection surface for placing the flexible printed circuit board thereon for visual inspection. The roller system includes a first roller for unwinding a flexible printed circuit board therefrom and a second roller for winding up the flexible printed circuit board therearound. The power system includes a driving device and a braking device. The driving device includes a torque motor engaging with the second roller to drive the second roller to roll. The braking device includes a detent engaging with the first roller to stop rolling of the first roller. The control system electrically connects to the power system for controlling the power system.

20 Claims, 6 Drawing Sheets

VISUAL INSPECTION APPARATUS FOR FLEXIBLE PRINTED CIRCUIT BOARDS

BACKGROUND

1. Technical Field

The present invention relates to inspection apparatuses, particularly to a visual inspection apparatus for flexible printed circuit boards.

2. Description of Related Art

Currently, flexible printed circuit boards can be manufactured using a roll-to-roll process which is a substitute of a typical sheet-by-sheet process. In the roll-to-roll process, a number of flexible printed circuit board units are manufactured using a copper clad substrate successively. The copper clad substrate is fabricated into the flexible printed circuit board units in a manner such that the copper clad substrate is wound up around a number of rollers to be performed a series of processes for manufacturing flexible printed circuit boards.

Generally, in the roll-to-roll process, after vias and electrical traces of each of the flexible printed circuit board units are fabricated, the vias and electrical traces of each of the flexible printed circuit board units are required to go under inspection so as to ensure the quality of the vias and electrical traces. Nowadays, an inspection process for inspecting the vias and electrical traces of each of the flexible printed circuit board units can be performed using an automatic optical inspection system or a manual visual inspection system.

However, the automatic optical inspection system is very expensive which greatly increases the overall cost of manufacturing flexible printed circuit boards. Currently, to save cost, the flexible printed circuit board (e.g., the copper clad substrate that has been fabricated into a number of flexible printed circuit board units) is generally inspected manually using the manual visual inspection system. However, a roller of the manual visual inspection system is generally driven to roll by a single motor. In the inspection process, the motor starts and stops frequently. When the motor starts, the flexible printed circuit board is pulled and a tension occurring on the flexible printed circuit board is large. When the motor stops, a tension occurring on the flexible printed circuit board disappears suddenly and the flexible printed circuit board is wrapped over the roller. Thus, the tension acts on the flexible printed circuit board is changed frequently, thereby damaging the electrical traces of the flexible printed circuit board. As a result, quality of each of the flexible printed circuit board units manufactured is inferior.

What is needed, therefore, is a visual inspection apparatus for inspecting the flexible printed circuit board by manually in a roll-to-roll process of manufacturing flexible printed circuit boards, thereby balancing the tension the flexible printed circuit board in the roll-to-roll process, and preventing the flexible printed circuit board from being damaged.

SUMMARY

One present embodiment provides a visual inspection apparatus for a flexible printed circuit board. The visual inspection apparatus includes a frame, an inspection station, a control system, a roller system and a power system. The inspection station is disposed on the frame. The inspection station has an inspection surface for placing the flexible printed circuit board thereon for visual inspection. The roller system is fixed on the frame. The roller system includes a first roller for unwinding a flexible printed circuit board therefrom and a second roller for winding up the flexible printed circuit board therearound. The power system is installed in the frame. The power system includes a driving device and a braking device. The driving device includes a torque motor engaging with the second roller to drive the second roller to roll. The braking device includes a detent engaging with the first roller to stop rolling of the first roller. The control system is installed in the frame. The control system electrically connects to the power system for controlling the power system.

BRIEF DESCRIPTION OF THE DRAWINGS

Many aspects of the present embodiment can be better understood with reference to the following drawings. The components in the drawings are not necessarily drawn to scale, the emphasis instead being placed upon clearly illustrating the principles of the present embodiment. Moreover, in the drawings, like reference numerals designate corresponding parts throughout the several views.

DETAILED DESCRIPTION OF THE EMBODIMENTS

Figure 1:
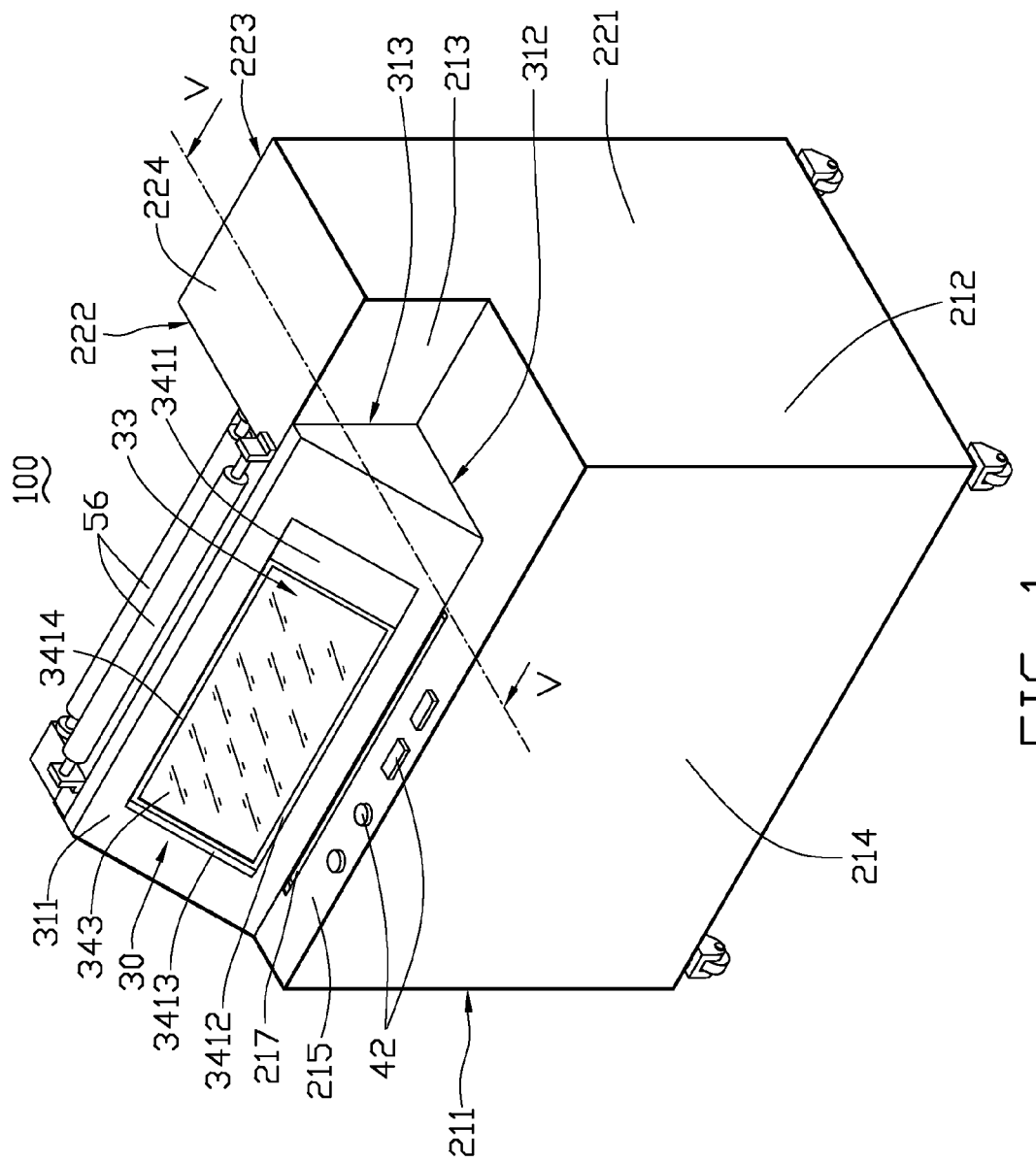
FIG. 1 is a front schematic view of a visual inspection apparatus for flexible printed circuit boards according to a present embodiment.

Embodiments will now be described in detail below and with reference to the drawings.

Referring to FIG. 1 to FIG. 5, an exemplary visual inspection apparatus 100 for flexible printed circuit boards according to a present embodiment is shown. The visual inspection apparatus 100 is configured for inspecting a flexible printed circuit board (e.g., a copper clad substrate that has been fabricated into a number of flexible printed circuit board units) by vision manually in a roll-to-roll process. The visual inspection apparatus 100 includes a frame 20, an inspection station 30, a control system 40, a roller system 50 and a power system 60.

The frame 20 is configured (i.e., arranged and structured) for receiving and installing the inspection station 30, the control system 40, the roller system 50 and the power system 60 thereof. Thus, the frame 20 can be a predetermined configuration according to structures and dimensions of the inspection station 30, the control system 40, the roller system 50 and the power system 60. In the present embodiment, the frame 20 includes a first frame 210 and a second frame 220 connecting with the first frame 210.

Figure 2:
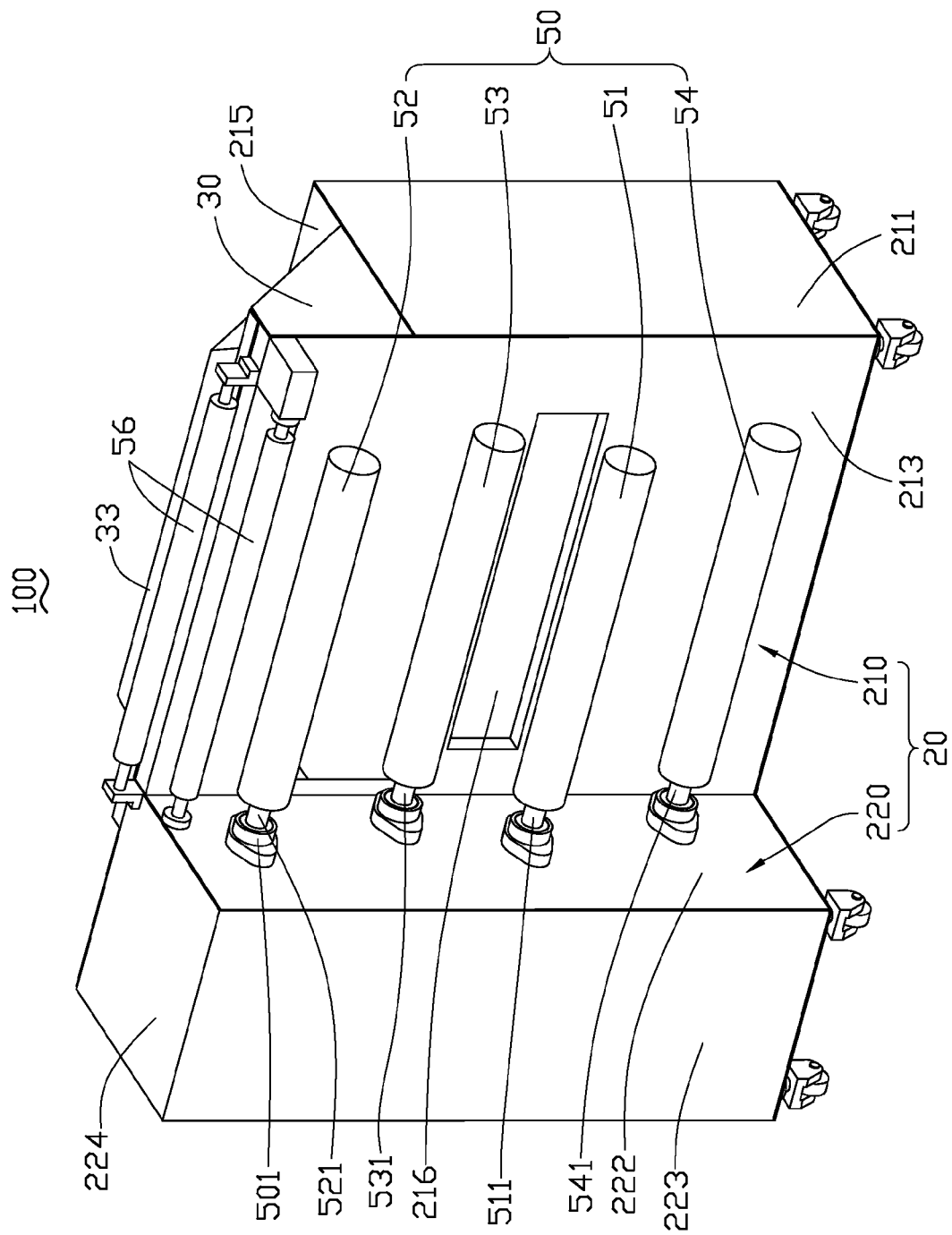
FIG. 2 is a rear schematic view of the visual inspection apparatus for flexible printed circuit boards according to the present embodiment.

The first frame 210 is configured (i.e., arranged and structured) for installing the inspection station 30 and the control system 40 thereof. Referring to FIG. 1 and FIG. 2, the first frame 210 has a first side plate 211, a second side plate 212 opposite to the first side plate 211, a third side plate 213, a fourth side plate 214 opposite to the third side plate 213, and a first top plate 215. The third side plate 213 and the fourth side plate 214 are located between the first side plate 211 and the second side plate 212. Two opposite end portions of the third side plate 213 respectively connect to end portion of the first side plate 211 and end portion of the second side plate 212 that are on one common side. Two opposite end portions of the fourth side plate 214 respectively connect to end portion of the first side plate 211 and end portion of the second side plate 212 that are on another common side. The first top plate 215 perpendicularly connects to the first side plate 211, the second side plate 212, the third side plate 213 and the fourth side plate 214, thereby forming the first frame 210. Preferably, the first side plate 211 is parallel to the second side plate 212, and the third side plate 213 is parallel to the fourth side plate 214. The first side plate 211, the second side plate 212, the third side plate 213, the fourth side plate 214 and the first top plate 215 perpendicularly connect to each other. Because the third side plate 213 is higher than the fourth side plate 214, a portion of the third side plate 213 protrudes from the first top plate 215. Therefore, the inspection station 30 can be fixed on the first top plate 215 contacting the third side plate 213.

Figure 4:
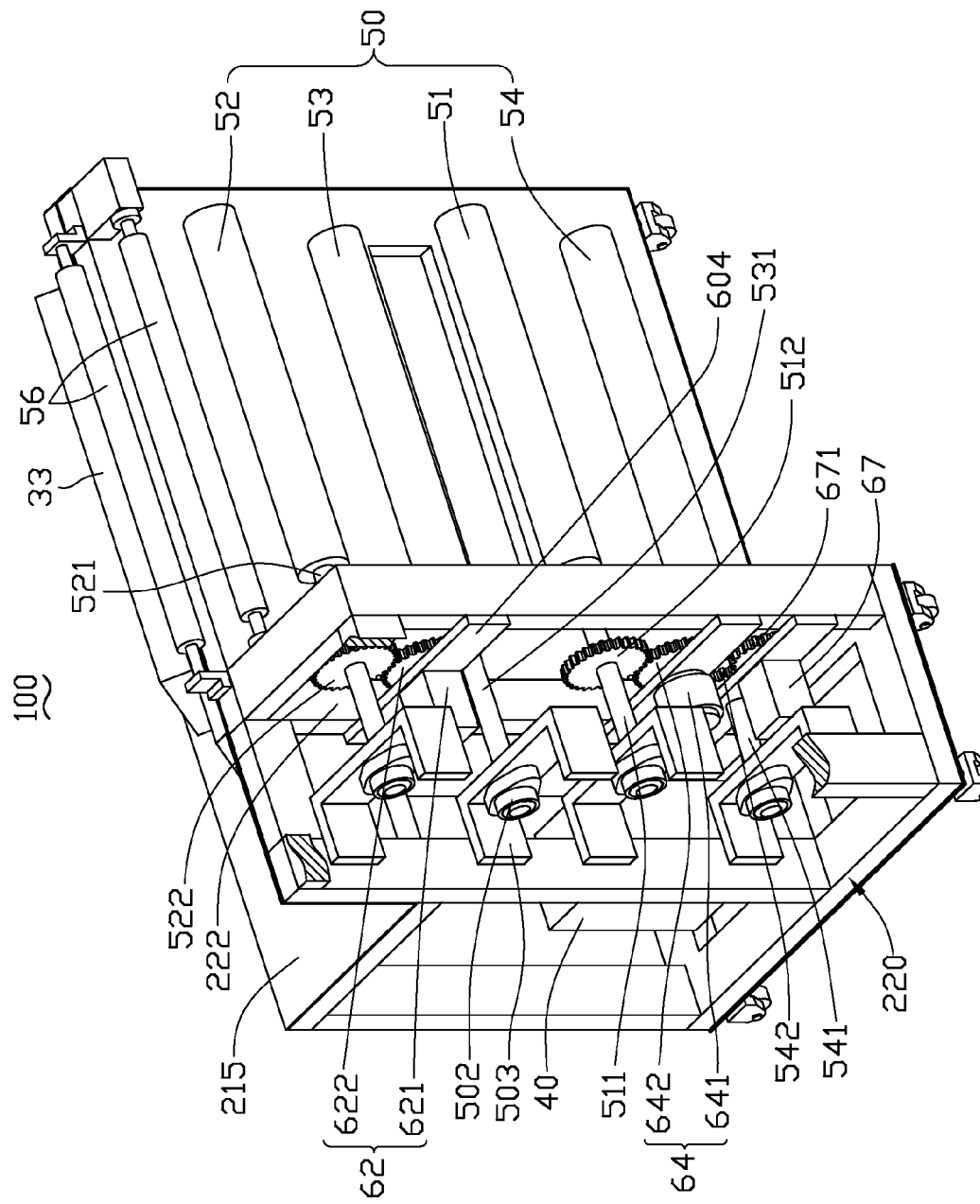
FIG. 4 is a partial cutaway view of a second frame of the visual inspection apparatus for flexible printed circuit boards according to the present embodiment.

Referring to FIG. 1 and FIG. 4, the first frame 210 is configured for receiving the control system 40 therein. In order to operate easily, a number of switches 42 of the control system 40 are located at the first top plate 215. It is understood that the switches 42 also can be located at any suitable positions of the first frame 210.

Referring to FIG. 1 and FIG. 2, the third side plate 213 defines a first cutout 216 and the first top plate 215 defines a second cutout 217. A lengthwise direction of the first cutout 216 and that of the second cutout 217 is perpendicular to a conveying direction of the flexible printed circuit board (i.e., a moving direction of the flexible printed circuit board in the inspecting process). A length of the first cutout 216 is larger than a width of the flexible printed circuit board (e.g., a width of the copper clad substrate that has been fabricated into a number of flexible printed circuit board units). A length of the second cutout 217 is also larger than a width of the flexible printed circuit board. Thus, the flexible printed circuit board can go through the first cutout 216 and the second cutout 217 in that order to arrive at the inspection station 30 for inspection.

The second frame 220 is configured (i.e., arranged and structured) for receiving the power system 60 and for installing and supporting the roller system 50. The second frame 220 is connected to the first frame 210. Referring to FIG. 1 and FIG. 2, the second frame 220 has a fifth side plate 221, a sixth side plate 222, a seventh side plate 223, and a second top plate 224. The fifth side plate 221 extends from the second side plate 212 of the first frame 210. The sixth side plate 222 is opposite to the fifth side plate 221 and connects to the third side plate 213 of the first frame 210. The seventh side plate 223 is between the fifth side plate 221 and the sixth side plate 222. Two opposite end portions of the seventh side plate 223 respectively connect to end portion the fifth side plate 221 and end portion of the sixth side plate 222 that are on one common side. The seventh side plate 223 is opposite to and parallel to the third side plate 213 of the first frame 210. The second top plate 224 perpendicularly connects to the fifth side plate 221, the sixth side plate 222, the seventh side plate 223 and the third side plate 213, thereby forming the second frame 220. A width of the seventh side plate 223 is less than that of the third side plate 213. Thus, the second frame 220 is connected to one end portion of the first frame 210 to form the frame 20.

The inspection station 30 is configured (i.e., arranged and structured ) for inspecting the flexible printed circuit board by vision. The inspection station 30 is fixed on the first top plate 215 and contacts the third side plate 213.

Referring to FIG. 1, in the present embodiment, the inspection station 30 has a configuration of a triangular prism. In detail, the inspection station 30 has a first surface 311, a second surface 312 and a third surface 313. The first surface 311 is configured for placing the flexible printed circuit board thereon for inspection. The first surface 311 defines an inspection surface (not shown) thereon. The flexible printed circuit board is placed onto the inspection surface to be inspected. The second surface 312 contacts the first top plate 215 and the third surface 313 contacts the third side plate 213 so that the inspection station 30 is fixed onto the first top plate 215.

The first surface 311 is slanted relative to the horizontal direction. The second surface 312 is parallel to the horizontal direction. An angle between the first surface 311 and the second surface 312 is less than 90 degrees (i.e., an acute angle). Because the second surface 312 contacts the horizontal first top plate 215 in the present embodiment, an angle between the first surface 311 and the horizontal is also less than 90 degrees. When an operator stands in front of the visual inspection apparatus 100, a sight line of the operator can arrives at an inspection position on the first surface 311. Therefore, the operator can inspect the flexible printed circuit board placed on the first surface 311 without bowing and lowering his/her head, thereby prevent the operator from tiredness during the inspection process. In the present embodiment, the angle between the first surface 311 and the second surface 312 is 45 degrees.

Advantageously, referring to FIG. 1, an illumination system 33 is disposed on the inspection station 30. The illumination system 33 is configured (i.e., arranged and structured) for illuminating the inspection surface (i.e., the first surface 311) of the inspection station 30 to improve inspection conditions.

Figure 3:
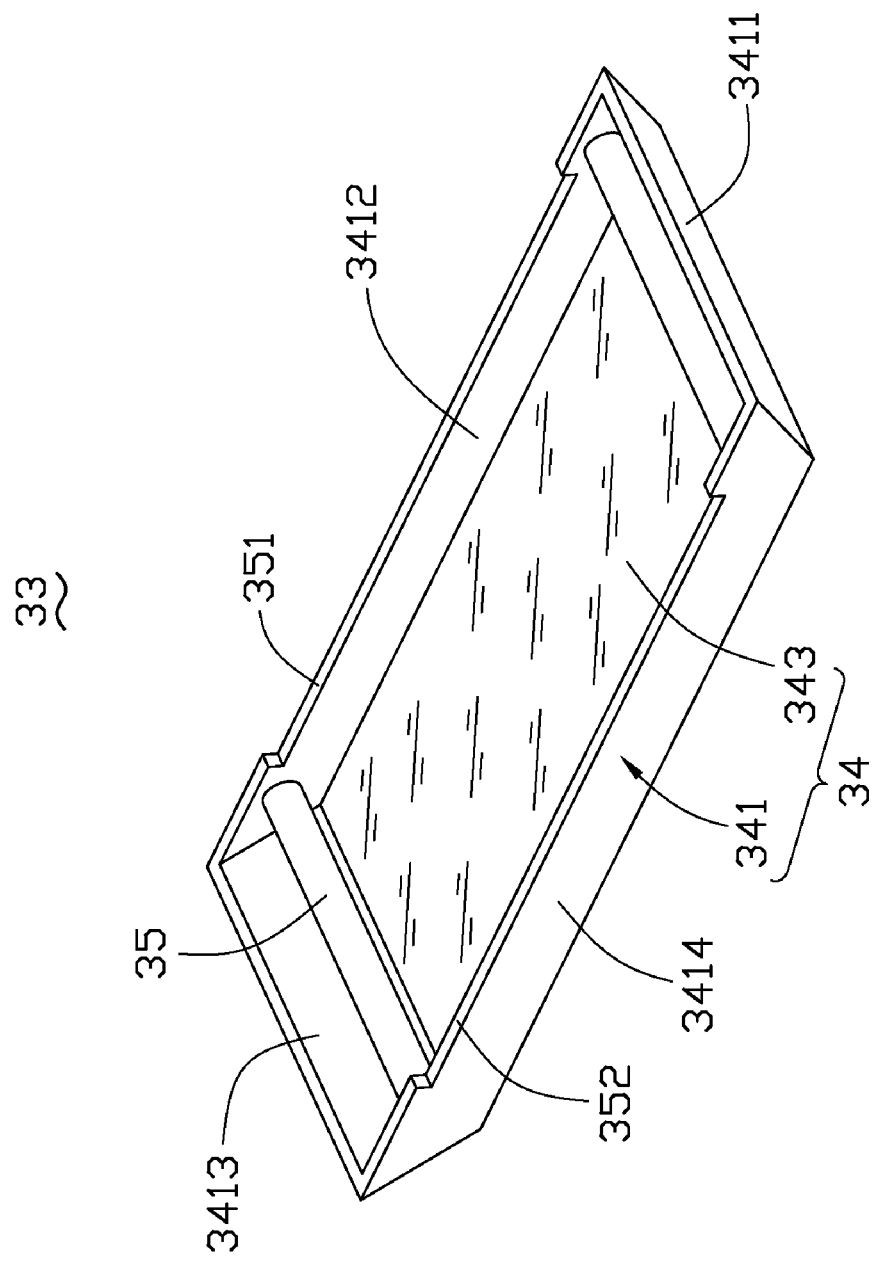
FIG. 3 is a schematic view of a illumination system of the visual inspection apparatus for flexible printed circuit boards according to the present embodiment.

Referring to FIG. 3, the illumination system 33 includes a light cover 34 and a light source 35. The light cover 34 includes a transparent portion 343 and a sidewall 341 connected to edges of the transparent portion 343.

The transparent portion 343 is comprised of a transparent material such as glass so that the operator can inspect the flexible printed circuit board through the transparent portion 343. The sidewall 341 is comprised of a reflecting material such as bright stainless steel so as to reflect light emitting from the light source 35. It is understood that the sidewall 341 also can be comprised of other materials. When the sidewall 341 is comprised of non-reflective materials, a reflecting coating is coated on an inner surface thereof. In the present embodiment, the transparent portion 343 is made of glass and the sidewall 341 is made of bright stainless steel.

The sidewall 341 of the light cover 34 includes a first sidewall 3411, a second sidewall 3412, a third sidewall 3413 opposite to the first sidewall 3411 and a fourth sidewall 3414 opposite to the second sidewall 3412. The first sidewall 3411, the second sidewall 3412, the third sidewall 3413 and the fourth sidewall 3414 connect to each other in the order written, and then connect to edges of the transparent portion 343 to form the light cover 34. An angle between the first sidewall 3411 and the transparent portion 343 is more than 90 degrees, for example, 135 degrees. An angle between the third sidewall 3413 and the transparent portion 343 is also more than 90 degrees, for example, 135 degrees. The second sidewall 3412 and the fourth sidewall 3414 perpendicularly connect to the transparent portion 343. The light cover 34 covers the inspection surface defined in the middle of the first surface 311 of the inspection station 30 so that the illumination system 33 is fixed onto the inspection station 30. It is understood that the light cover 34 can be other desired configurations.

Additionally, the second sidewall 3412 defines a third cutout 351 and the fourth sidewall 3414 defines a fourth cutout 352 corresponding to the third cutout 351. Thus, when the light cover 34 covers the first surface 311 of the inspection station 30, the light cover 34 cannot block a transmitting motion of the flexible printed circuit board. That is, the flexible printed circuit board can go through the first cutout 216, the third cutout 351, the fourth cutout 352 and the second cutout 217 in the order written so as to arrive at the first surface 311 of the inspection station 30 for inspection. A lengthwise direction of the third cutout 351 and that of the fourth cutout 352 is perpendicular to a conveying direction of the flexible printed circuit board. A length of the third cutout 351 is more than a width of the flexible printed circuit board. A length of the fourth cutout 352 is also more than a width of the flexible printed circuit board. Therefore, the second sidewall 3412 and the fourth sidewall 3414 each have an enough space to define the third cutout 351 and the fourth cutout 352 respectively.

The light source 35 is installed in a space between the light cover 34 and the first surface 311 of the inspection station 30. In the present embodiment, two light sources 35 are respectively disposed in the light cover 34 and located at the two opposite ends of the transparent portion 343. Two opposite ends of each of the two light sources 35 connect to the second sidewall 3412 and the fourth sidewall 3414 respectively. It is noted that the light source 35 can be disposed onto the first surface 311 of the inspection station 30. However, the light source 35 cannot block the light of sight of the operator to inspect the flexible printed circuit board. The light emitting from the light source 35 is reflected by the sidewall 34, thereby effectively increasing the brightness of the light illuminating onto the first surface 311 of the inspection station 30.

Figure 5:
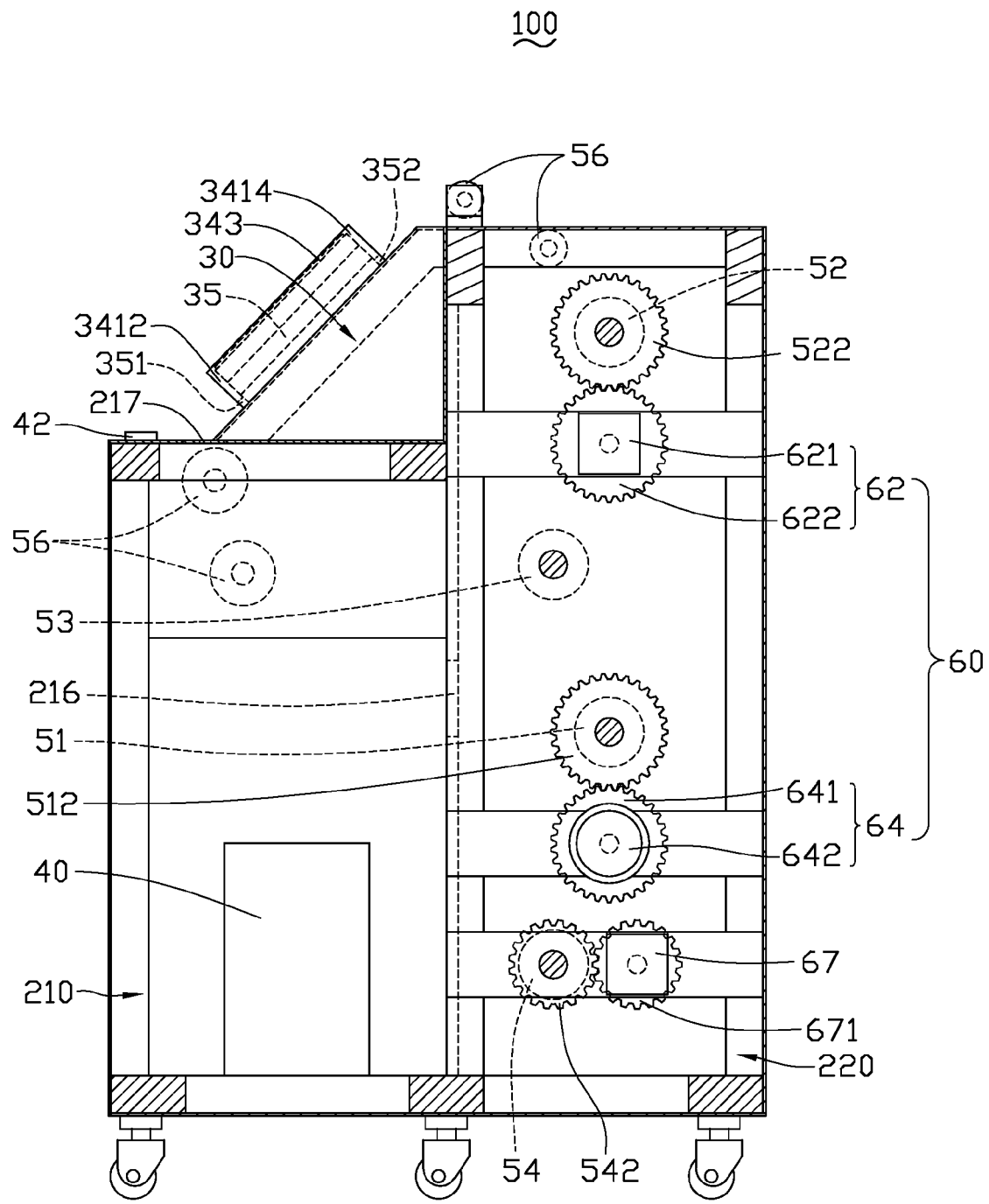
FIG. 5 is a schematic, cross-sectional view of the visual inspection apparatus for flexible printed circuit boards in FIG. 1 as viewed along line V-V.

Referring to FIG. 1, FIG.4 and FIG. 5, the control system 40 is configured for controlling the power system 60. The control system 40 is installed in the first frame 210. The control system 40 electrically connects to the switches 42 disposed on the first top plate 215 of the first frame 210. The controlling system 40 electrically connects to the power system 60 so as to control the power system 60.

Further, the controlling system 40 electrically can connect to the light source 35 of the illumination system 33 for controlling the illumination system 33.

Referring to FIG. 2 and FIG. 4, the roller system 50 is configured (i.e., arranged and structured) for transmitting the flexible printed circuit board. The roller system 50 is fixed on the sixth side plate 222 of the second frame 220. A lengthwise direction of each roller of the roller system 50 is parallel to the third side plate 213 of the first frame 210.

In the present embodiment, the roller system 50 includes a first roller 51, a second roller 52, a third roller 53 and a fourth roller 54. The second roller 52, the third roller 53, the first roller 51 and the fourth roller 54 are parallel to each other and are arranged in the order written from top to bottom on the sixth side plate 222 of the second frame 220. The third roller 53 is located between the second roller 52 and the first roller 51. The third roller 53 is adjacent to the second roller 52. The fourth roller 54 is located below and adjacent to the first roller 51.

The first roller 51 for unwinding the flexible printed circuit board therefrom and the second roller 52 are configured for winding up the flexible printed circuit board therearound. The third roller 53 and the fourth roller 54 each are configured for winding up a separating film therearound. The separating film is configured for protecting the electrical traces of the flexible printed circuit board. The third roller 53 is configured for winding up the separating film laminated with the flexible printed circuit board that has been inspected. The fourth roller 54 is configured for winding up the separating film laminated with the flexible printed circuit board to be inspected. It is noted that the third roller 53 and the fourth roller 54 can be selectively installed on the second frame 220 when the corresponding separating film is not used in the inspection process.

The first roller 51 has a first rolling shaft 511. The second roller 52 has a second rolling shaft 521. The third roller 53 has a third rolling shaft 531. The fourth roller 54 has a fourth rolling shaft 541. The first rolling shaft 511, the second rolling shaft 521, the third rolling shaft 531 and the fourth rolling shaft 541 are engaged in a respective shaft bearing 501 fixed on the sixth side plate 222. One end portion of each of the first rolling shaft 511, the second rolling shaft 521, the third rolling shaft 531 and the fourth rolling shaft 541 is inside the second frame 220. The other end portion of each of the first rolling shaft 511, the second rolling shaft 521, the third rolling shaft 531 and the fourth rolling shaft 541 is outside the second frame 220. Thus, the first roller 51, the second roller 52, the third roller 53 and the fourth roller 54 are disposed on the outside the second frame 220. A lengthwise direction of each of the first roller 51, the second roller 52, the third roller 53 and the fourth roller 54 is parallel to the third side plate 213 of the first frame 210.

Advantageously, one end portion of each of the first rolling shaft 511, the second rolling shaft 521, the third rolling shaft 531, and the fourth rolling shaft 541 can be engaged in a respective shaft bearing 502 fixed in the first fixing member 503 fixed on the fifth side plate 221. Thus, the first roller 51, the second roller 52, the third roller 53 and the fourth roller 54 can be stably fixed on the second frame 220.

The first rolling shaft 511 inside the second frame 220 is engaged to a first gear 512. The second rolling shaft 521 inside the second frame 220 is engaged to a second gear 522. The fourth rolling shaft 541 inside the second frame 220 is engaged to a third gear 542. The first gear 512, the second gear 522 and the fourth gear 542 are configured for engaging with the corresponding gear of the power system 60 so that the power system 60 can drive the first roller 51, the second roller 52 and the fourth roller 54 to roll.

Advantageously, according to the configuration of the frame 20, a number of turning rollers 56 can be disposed on the frame 20. The turning rollers 56 are configured for changing the conveying direction of the flexible printed circuit board transmitting from the first roller 51 to the second roller 52. In the present embodiment, four turning rollers 56 are disposed on the frame 20. Referring to FIG. 4 and FIG. 5, two turning rollers 56 are installed in the first frame 210. A lengthwise direction of each of the two turning rollers 56 is parallel to that of the first roller 51 and the second roller 52. The two turning rollers 56 in the first frame 210 are configured for moving the flexible printed circuit board to the inspection station 30. In addition, other two turning rollers 56 are fixed at the top of the third side plate 213 and close to the inspection station 30. A lengthwise direction of each of the other two turning rollers 56 is also parallel to that of the first roller 51 and the second roller 52. The other two turning rollers 56 are configured for moving the flexible printed circuit board to the second roller 52.

Referring to FIG. 4 and FIG. 5, the power system 60 is configured for supplying power to the roller system 50 to start or stop rolling. The power system 60 includes a driving device 62 and a braking device 64. The driving device 62 is configured for driving the roller system 50 to roll. The braking device 64 is configured for stopping rolling of the roller system 50. The driving device 62 and the braking device 64 are installed in the second frame 220. The driving device 62 and the braking device 64 are fixed on the sixth side plate 222 via the second fixing member 604 fixed on the sixth side plate 222.

The driving device 62 includes a torque motor 621 and a fourth gear 622 engaged with the torque motor 621. The torque motor 621 is configured for driving the second roller 52 to roll. In detail, the fourth gear 622 is engaged with the second gear 522 of the second roller 52. When the torque motor 621 drives the fourth gear 622 to roll, the rolling of the fourth gear 622 drives the second gear 522 of the second roller 52 to roll correspondingly. Thus, the second roller 52 is driven to roll.

The braking device 64 includes a detent 641 and a fifth gear 642 engaged with the detent 641. The detent 641 is configured for stopping rolling of the first roller 51. In detail, the fifth gear 642 is engaged with the first gear 512 of the first roller 51. When the detent 641 stops rolling of the fifth gear 642, the fifth gear 642 blocks the rolling of the second gear 522 engaged with the fifth gear 642 correspondingly. Thus, the first roller 51 stops rolling.

The driving device 62 and the braking device 64 cooperate with each other so as to control movement of the first roller 51 and the second roller 52, thereby balancing a tension occurring on the flexible printed circuit board wound up around the first roller 51 and the second roller 52. Thus, the tension occurring on the flexible printed circuit board can maintain stability in the entire inspection process, thereby preventing the electrical traces of the flexible printed circuit board from being damaged.

Additionally, a driving motor 67 and a sixth gear 671 engaged with the driving motor 67 are installed in the second frame 220. The driving motor 67 is also fixed on the sixth side plate 222 via the corresponding second fixing member 604. The sixth gear 671 is engaged with the third gear 542 of the fourth roller 54. When the driving motor 67 drives the sixth gear 671 to roll, the rolling of the sixth gear 671 drives the third gear 542 of the fourth roller 54 to roll correspondingly. Thus, the fourth roller 52 is driven to roll. It is understood that the fourth roller 54 can connect to the second roller 52 via a chain wheel, and thus movements of the fourth roller can be driven by movements of the second roller 52.

Figure 6:
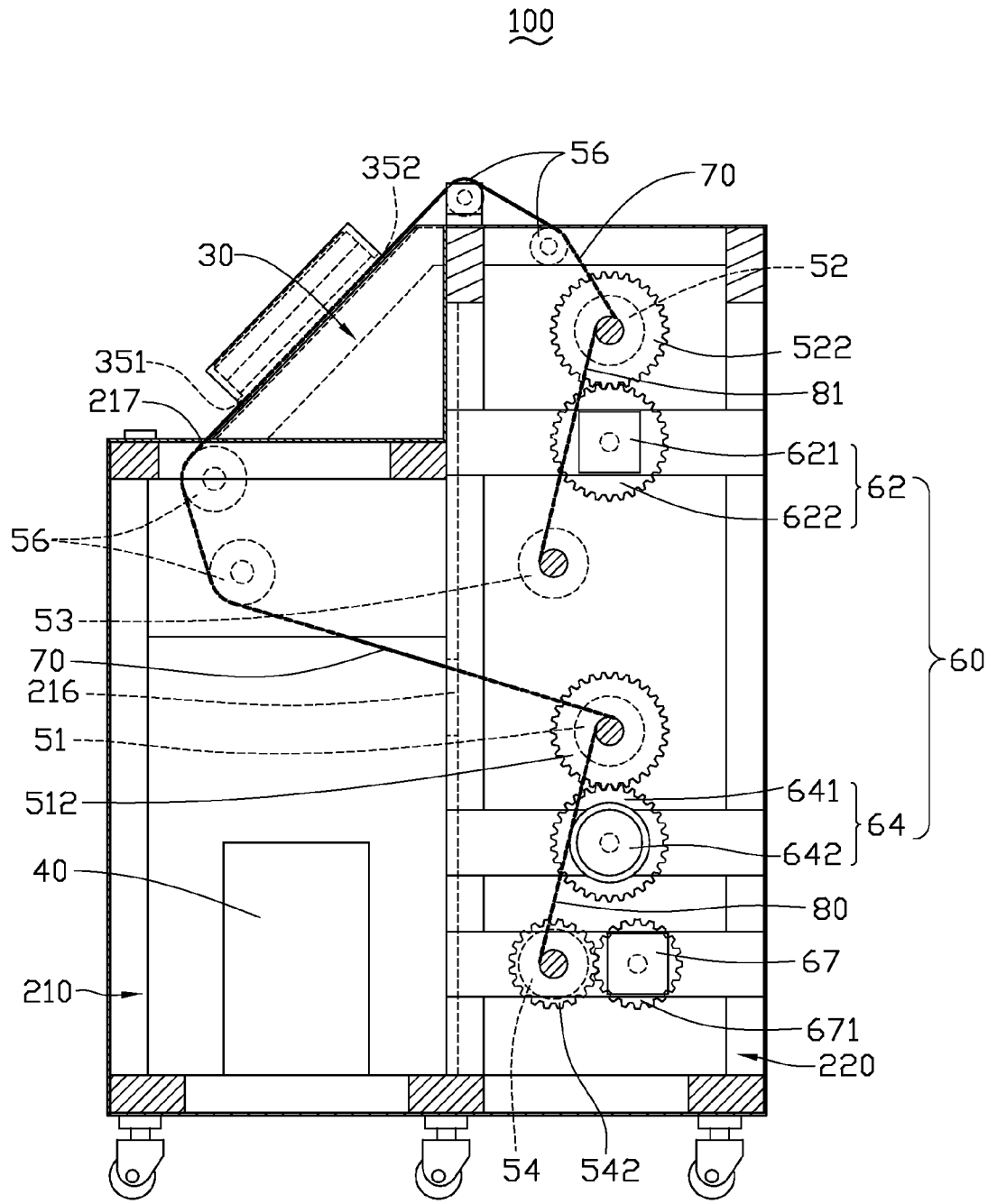
FIG. 6 is a schematic view of using the visual inspection apparatus for flexible printed circuit boards in FIG. 5.

Referring to FIG. 6, a flexible printed circuit board 70 (e.g., a copper clad substrate that has been fabricated into a number of flexible printed circuit board units) is inspected using the visual inspection apparatus 100. The flexible printed circuit board 70 is laminated with a first separating film 80. The first separating film 80 is configured for protecting the electrical traces of the flexible printed circuit board 70, when the flexible printed circuit board 71 is wound up around the first roller 51.

The flexible printed circuit board 70 laminated with the first separating film 80 is wound up around the first roller 51. In order to locate the flexible printed circuit board 70 and the first separating film 80, the flexible printed circuit board 70 is unwound from the first roller 51 and is separated from the first separating film 80. The flexible printed circuit board 70 unwound from the first roller 51 goes through the first frame 210. In detail, the flexible printed circuit board 70 unwound from the first roller 51 at first goes through the first cutout 216, and is then moved by the turning rollers 56 and goes through the second cutout 217. Then, the flexible printed circuit board 70 out of the first frame 210 from the second cutout 217 goes through the third cutout 351 and the fourth cutout 352 so that the flexible printed circuit board 70 goes through the illumination system 33 to arrive at the inspection station 30 fixed on the first frame 210. The flexible printed circuit board 70 out of the fourth cutout 352 is moved by the turning rollers 56 and is wound up around the second roller 52.

Advantageously, a second separating film 81 is wound up around the third roller 53. The second separating film 81 is also configured for protecting electrical traces of the flexible printed circuit board 70, when the flexible printed circuit board 70 is wound up around the second roller 52. The second separating film 81 unwound from the third roller 53 is laminated with the flexible printed circuit board 70. The flexible printed circuit board 70 laminated with the second separating film 81 is wound up around the second roller 52. Meanwhile, the first separating film 80 unwound from the first roller 51 is wound up around the fourth roller 54 correspondingly.

In the inspection process, firstly, the driving device 62 activates to drive the second roller 52 to wind up around the flexible printed circuit board 70. Therefore, the second roller 52 drives the flexible printed circuit board 70 to transmit. Because the braking device 64 is shut-off at the same time, the transmitting motion of the flexible printed circuit board 70 drives the first roller 51 to roll automatically and the flexible printed circuit board 70 is unwound from the first roller 51 successively. Thus, inspection areas of the flexible printed circuit board 70 can arrive at the inspection station 30 one by one and be placed onto the first surface 311 of the inspection station 30 to be inspected.

Secondly, when an inspection area of the flexible printed circuit board 70 arrives at the inspection station 30, the braking device 64 activates to stop rolling of the first roller 51. Thus, the transmitting motion of the flexible printed circuit board 70 stops immediately. The inspection area of the flexible printed circuit board 70 is stationary close to the inspection station 30. The operator standing in front of the inspection station 30 can inspect the stationary inspection area of the flexible printed circuit board 70 by vision. In order to maintain a secure and stable inspection process, the driving device 62 cooperates with the braking device 64 to control and adjust the first roller 51 and the second roller 52. In detail, when the braking device 64 stops, the driving device 62 is still working. That is, the first roller 51 stops rolling and the second roller 52 still rolls. Therefore, the flexible printed circuit board 70 undergoes a lager tension caused by a fastening force of the first roller 51 and a pulling force of the second roller 52. Instantaneously, the flexible printed circuit board 70 is tightly wound up around the first roller 51 and the second roller 52. Simultaneously, the torque motor 621 reduces its rotate speed immediately according to the tension occurring on the flexible printed circuit board 70. Thus, the rolling speed of the second roller 52 decreases immediately so as to reduce the pulling force of the second roller 52 occurring on the flexible printed circuit board 70 in time. When the pulling force of the second roller 52 reduces to a suitable value to balance the fastening force of the first roller 51, the tension occurring on the flexible printed circuit board 70 wound up around the first roller 51 and the second roller 52 is decreased immediately, thereby winding up the flexible printed circuit board 70 around the first roller 51 and the second roller 52 under a suitable tension, and preventing the electrical traces of the flexible printed circuit board 70 from being damaged. As a result, the inspection area of the flexible printed circuit board 70 can be stably stationary close to the inspection station 30 and to be inspected accurately.

Thirdly, after the inspection area of the flexible printed circuit board 70 is inspected by the operator, the braking device 64 is shut off, and the fastening force of the first roller 51 is decreased. At the same time, the driving device 62 is still working, and the pulling force of the second roller 52 still exists. The pulling force of the second roller 52 loses a force balance of the fastening force of the first roller 51. The driving device 62 drives the second roller 52 to wind up around the flexible printed circuit board 70. The transmitting motion of the flexible printed circuit board 70 then drives the first roller 51 to roll again. When the first roller 51 rolling again, the force occurring on the flexible printed circuit board 70 wound up around the first roller 51 and the second roller 52 loses balance and the tension occurring on the flexible printed circuit board 70 is reduced immediately. Instantaneously, the flexible printed circuit board 70 is wound up around the first roller 51 and the second roller 52 loosely. Simultaneously, the torque motor 621 increases its rotate speed immediately according to the tension of the flexible printed circuit board 70 in time. Thus, the rolling speed of the second roller 52 increases immediately so as to increase the pulling force of the second roller 52 occurring on the flexible printed circuit board 70 in time, thereby increasing the fastening force of the first roller 51 balancing with the pulling force of the second roller 52. When the pulling force of the second roller 52 increases to a suitable value, the tension occurring on the flexible printed circuit board 70 wound up around the first roller 51 and the second roller 52 can be increased immediately, thereby winding up the flexible printed circuit board 70 around the first roller 51 and the second roller 52 under a suitable tension, and preventing the electrical traces of the flexible printed circuit board 70 from damage.

When the other one inspection area of the flexible printed circuit board 70 arrives at the first surface 311 of the inspection station 30. The operator can start and stop the braking device 64 repeatedly as described above. In the entire roll-to-roll inspection process of the flexible printed circuit board 70, the flexible printed circuit board 70 undergoes a stable tension at all time due to the adjustment of the rotate speed of the torque motor 621 of the driving device 62 in time. Therefore, in the inspection process using the visual inspection apparatus 100, the electrical traces of the flexible printed circuit board 70 cannot be damaged.

While certain embodiments have been described and exemplified above, various other embodiments will be apparent to those skilled in the art from the foregoing disclosure. The present invention is not limited to the particular embodiments described and exemplified but is capable of considerable variation and modification without departure from the scope of the appended claims.

What is claimed is:

1. A visual inspection apparatus for a flexible printed circuit board, comprising:
    a frame;
    an inspection station disposed on the frame, the inspection station having an inspection surface for placing the flexible printed circuit board thereon for visual inspection;
    a roller system fixed on the frame, the roller system comprising a first roller for unwinding a flexible printed circuit board therefrom and a second roller for winding up the flexible printed circuit board therearound;
    a power system installed in the frame, the power system comprising a driving device and a braking device, the driving device comprising a torque motor engaging with the second roller to drive the second roller to roll, the braking device engaging with the first roller for stopping rolling of the first roller; and
    a control system installed in the frame, the control system electrically connecting to the power system for controlling the power system.

2. The visual inspection apparatus as claimed in claim 1, wherein the frame comprises a first frame and a second frame, the first frame is configured for installing the inspection station thereon and receiving the control system therein, the second frame is configured for receiving the power system therein and for installing and supporting the roller system thereoutside.

3. The visual inspection apparatus as claimed in claim 2, wherein the first frame defines a first cutout and a second cutout so that the flexible printed circuit board unwound from the first roller goes through the first frame to arrive at the inspection station.

4. The visual inspection apparatus as claimed in claim 3, wherein the torque motor comprises a gear meshed with the second roller.

5. The visual inspection apparatus as claimed in claim 3, wherein the braking device comprises a gear meshed with the first roller.

6. The visual inspection apparatus as claimed in claim 3, wherein the roller system further comprises a third roller and a fourth roller, the second roller, the third roller, the first roller and the fourth roller are parallel to each other and are arranged in that order from an upside of the frame to a downside of the frame, the third roller is configured for winding up a separating film.

7. The visual inspection apparatus as claimed in claim 5, wherein the fourth roller is adjacent to the first roller and is configured for winding up a first separating film laminated with the flexible printed circuit board to be inspected.

8. The visual inspection apparatus as claimed in claim 7, wherein the third roller is adjacent to the second roller and is configured for winding up a second separating film laminated with the flexible printed circuit board that has been inspected.

9. The visual inspection apparatus as claimed in claim 8, wherein the fourth roller is connected to the second roller so that rolling of the second roller drives the fourth roller to roll.

10. The visual inspection apparatus as claimed in claim 8, further comprising a driving motor engaged with the fourth roller for driving the fourth roller to roll 11. The visual inspection apparatus as claimed in claim 6, wherein the roller system further comprises a plurality of turning rollers disposed on the frame so as to convey the flexible printed circuit board from the first roller to the second roller.

12. The visual inspection apparatus as claimed in claim 3, wherein the inspection station has a configuration of triangular prism, the inspection station comprises a first surface, a second surface and a third surface, the first surface having the inspection surface defined thereon.

13. The visual inspection apparatus as claimed in claim 12, wherein the first surface is slanted relative to the horizontal direction.

14. The visual inspection apparatus as claimed in claim 13, wherein an angle between the first surface and the horizontal direction is 45 degrees.

15. The visual inspection apparatus as claimed in claim 12, further comprising an illumination system disposed on the inspection station for illuminating the inspection surface of the inspection station.

16. The visual inspection apparatus as claimed in claim 15, wherein the illumination system comprises a light cover and a light source, the light cover has a transparent portion and a sidewall connecting edges of the transparent portion, the light cover covers the inspection surface of the inspection station, the light source is installed between the light cover and the inspection surface of the inspection station.

17. The visual inspection apparatus as claimed in claim 16, wherein the sidewall comprises a first sidewall, a second sidewall, a third sidewall opposite to the first sidewall and a fourth sidewall opposite to the second sidewall, an angle between the first sidewall and the transparent portion and that between the third sidewall and the transparent portion each are more than 90 degrees, the second sidewall and the fourth sidewall each being perpendicular to the transparent portion, the second sidewall and the fourth sidewall respectively defines a third cutout and a fourth cutout so that the flexible printed circuit board out of the first frame from the second cutout goes through the illumination system to arrive at the inspection station.

18. The visual inspection apparatus as claimed in claim 17, wherein the sidewall is comprised of reflecting materials.

19. The visual inspection apparatus as claimed in claim 17, wherein the sidewall has a reflecting coating formed on an inner surface thereof.

20. A flexible printed circuit board inspection apparatus comprising:
- a first roller for unwinding a to-be-inspected flexible printed circuit board therefrom;
- a second roller for winding up the flexible printed circuit board therearound;
- a conveying assembly for conveying unwound part of the flexible printed circuit board from the first roller to the second driven roller;
- a torque motor engaged with the second driven roller for driving the second roller to roll, thereby winding up the flexible printed circuit board around the second roller; and
- a braking device engaged with the first roller for stopping rolling of the first roller.

* * * * *